US00PP31356P2

(12) United States Plant Patent
Kleinwee

(10) Patent No.: US PP31,356 P2
(45) Date of Patent: Jan. 14, 2020

(54) ***CHRYSANTHEMUM* PLANT NAMED 'CIFZ0067'**

(50) Latin Name: *Chrysanthemum x morifolium*
Varietal Denomination: CIFZ0067

(71) Applicant: SYNGENTA PARTICIPATIONS AG, Basel (CH)

(72) Inventor: Theodorus Cornelis Maria van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/350,890

(22) Filed: Jan. 29, 2019

(51) Int. Cl.
*A01H 5/02* (2018.01)
*A01H 6/14* (2018.01)

(52) U.S. Cl.
USPC ..... Plt./286
CPC ..... *A01H 6/14* (2018.05)

(58) Field of Classification Search
USPC ..... Plt./286
CPC ..... A01H 5/02
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0067' particularly distinguished by its medium size plant with round mound plant habit, a medium size (2.0 inch), bright lavender ray floret color and a natural season response mid to late September.

1 Drawing Sheet

Figure 1:
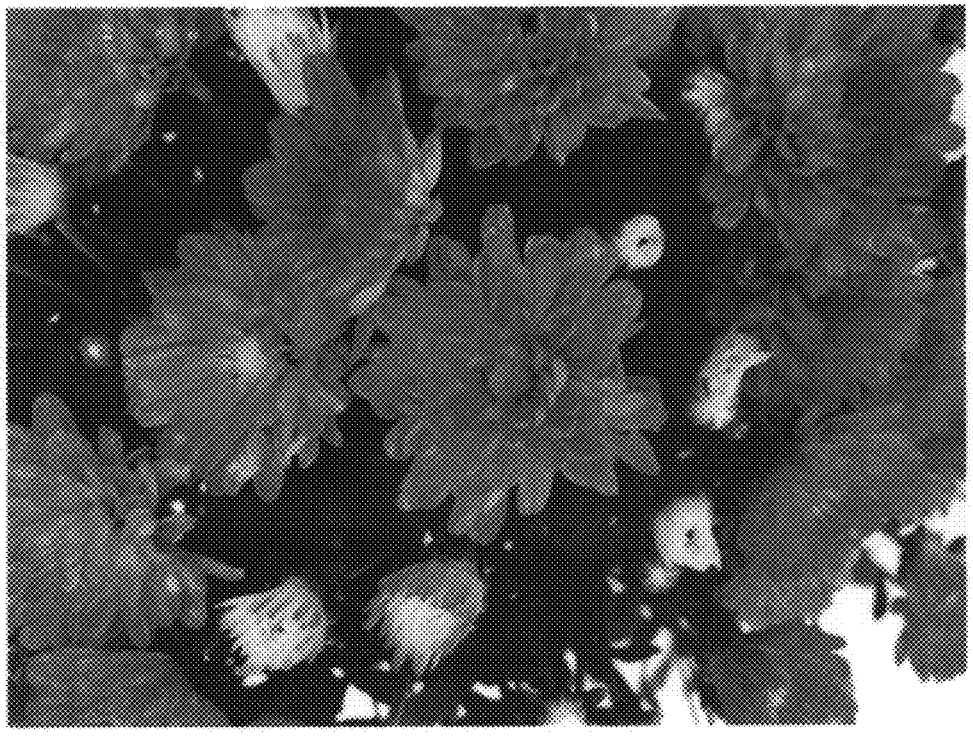

Latin name of the genus and species of the plant claimed: *Chrysanthemum x morifolium.*

Varietal denomination: 'CIFZ0067'.

BACKGROUND OF THE NEW PLANT

The present invention comprises a new *Chrysanthemum*, botanically known as *Chrysanthemum x morifolium*, and hereinafter referred to by the variety name 'CIFZ0067'.

'CIFZ0067' is a product of a planned breeding program. The new cultivar has medium size plant with round mound plant habit, a medium size (2.0 inch), bright lavender flower color and a natural season response mid to late September 'CIFZ0067' originated from a cross made in December 2010 in Tenjo, Columbia. Seeds were sown in June 2012 in Enkhuizen, The Netherlands and 'CIFZ0067' was selected from the resulting population on Oct. 24, 2012 in Enkhuizen, The Netherlands The female parent was the variety 'Syhes Hored', U.S. Plant Pat. No. 23, 519

When compared to the female parent, 'CIFZ0067' has:

A similar inflorescence size with more disc florets and inflorescence color is bright lavender not red like 'Syhes Hored'.

A similar blackcloth and natural season response as 'Syhes Hored' except when it is hot and then it flowers slower than 'Syhes Hored'.

A similar plant size but rounder plant habit than 'Syhes Hored'.

The male parent was the unnamed seedling '06-M281'.

When compared to the male parent, 'CIFZ0067' has:

A similar inflorescence type, but bit larger in size and bright lavender color not pinky white like the male parent.

A half week faster blackcloth response and similar natural season response as the male parent.

Is similar in plant size and plant habit as the male parent.

Is a sturdier plant/less apt to split than the male parent.

The first act of asexual reproduction of 'CIFZ0067' was accomplished when vegetative cuttings were propagated from the initial selection in January 2013 in Enkhuizen, the Netherlands.

BRIEF SUMMARY OF INVENTION

Horticultural examination of plants grown from cuttings of the plant initiated in January 2014 and continuing thereafter, has demonstrated that the combination of characteristics as herein disclosed for 'CIFZ0067' are firmly fixed and are retained through successive generations of asexual reproduction.

'CIFZ0067' has not been observed under all possible environmental conditions. The phenotype may vary significantly with variations in environment such as temperature, light intensity and day length.

A Plant Breeder's Right for this cultivar has not yet been applied for. 'CIFZ0067' has not been made publicly available prior to the effective filing date of this application, notwithstanding any disclosure that may have been made less than one year prior to the effective filing date of this application by the inventor or another who obtained 'CIFZ0067' directly from the inventor.

The following traits have been repeatedly observed and are determined to be basic characteristics of the new variety. The combination of these characteristics distinguishes this Chrysanthemum as a new and distinct variety.

BRIEF DESCRIPTION OF THE PHOTOGRAPHS

The accompanying photographic drawings show typical inflorescence and foliage characteristics of 'CIFZ0067' with colors being as true as possible with an illustration of this type. The photographic drawings show in FIG. 1 a close view of inflorescence of the new variety and in FIG. 2 a flowering plant from an outdoor trial.

Figure 2:
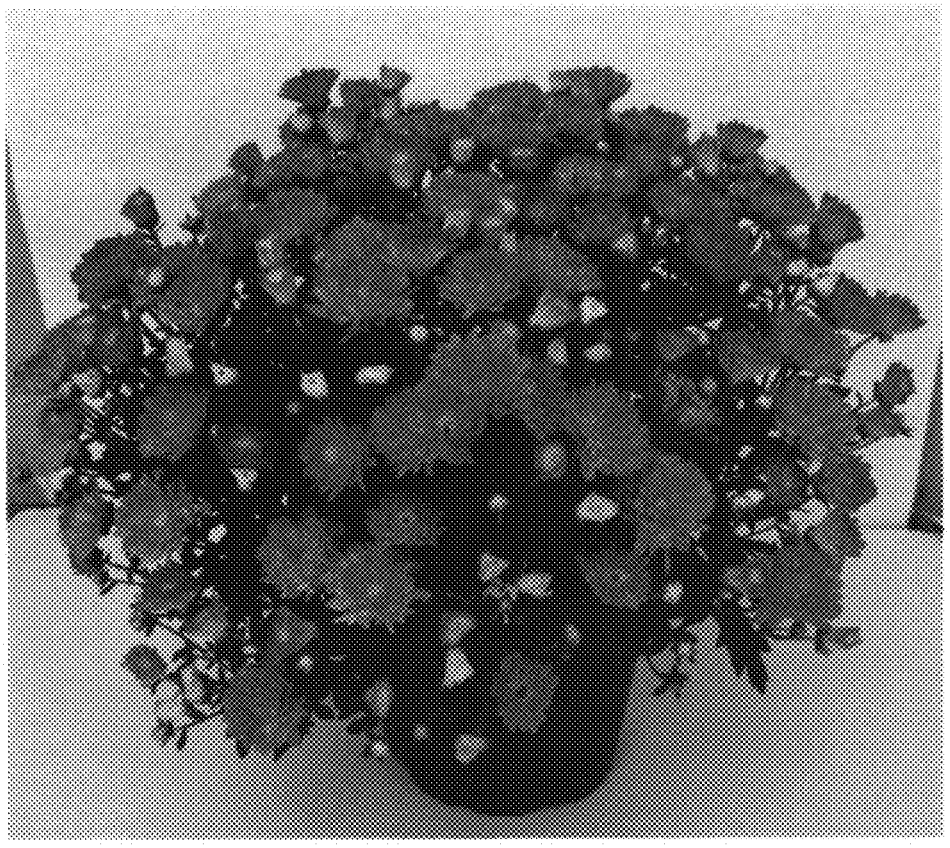

The aforementioned photographs: FIG. 1, as well as FIG. 2 were taken in August 2018 both showing a plant from the same blackcloth indoor trial in Gilroy, Calif.

These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif. in August 2018 on the plants from the aforementioned trial.

Color references are made to The Royal Horticultural Society Colour Chart (RHS) 2015.

TABLE 1

DIFFERENCES BETWEEN THE NEW VARIETY 'CIFZ0067' AND TWO MOST SIMILAR VARIETIES:

| | 'CIFZ0067' | 'Yoursula', U.S. Plant Pat. No. 13,641 |
|---|---|---|
| Flowering response (blackcloth): | Similar | Similar |
| Flowering response (natural): | Similar | Similar |
| Ray floret color: | Brighter shade of lavender color | Color not as bright |
| Flowering uniformity | Not very uniformly flowering | Very uniform flowering |
| Inflorescence type, size: | Similar inflorescence type with larger inflorescence size | Similar inflorescence type with smaller inflorescence size |
| Plant habit or size: | Similar in plant habit with similar or bit larger overall plant size | Similar in plant habit with similar or bit smaller overall plant size |

| | 'CIFZ0067' | 'Fimmdaypi', U.S. Plant Pat. No. 27,068 |
|---|---|---|
| Flowering response (blackcloth): | A few days faster to flower in blackcloth | A few days faster to flower in blackcloth |
| Flowering response (natural): | Similar | Similar |
| Colour fading | Less fading | More fading |
| Ray floret color: | Bright lavender color | More dull lavender color |
| Inflorescence longevity: | Has longer lasting inflorescence | Has shorter lasting inflorescence |
| Inflorescence size and type: | Similar inflorescence size, with more disk florets | Similar inflorescence size, with less disk florets |
| Plant habit or size: | Similar plant habit with larger plant size | Similar plant habit with smaller plant size |

Plant:

*Form, growth and habit.*—Herbaceous garden-type, stems upright and outwardly spreading, freely branching, strong and moderately vigorous growth habit.

*Plant height* (*above soil*).—4-11 cm.

*Plant height* (*inflorescence included*).—13-27 cm.

*Plant width.*—37-40 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137C.

*Immature leaf, color lower surface.*—RHS 139C.

*Mature leaf, color, upper surface.*—Between RHS 137B.

*Mature leaf, color lower surface.*—Closest to RHS 138B.

*Length.*—4.5-4.9 cm.

*Width.*—3.5-3.7 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138A.

*Color of veins, lower surface.*—RHS N138B.

*Pattern of veining.*—Palmate.

*Petiole color.*—RHS 138A.

*Petiole length.*—0.8-1.1 cm.

*Diameter.*—0.3 cm.

*Texture.*—Covered with bifid hairs.

Stem:

*Quantity of main branches per plant.*—6-8.

*Color of stem.*—RHS 137D.

*Length of stem.*—7.0-8.0 cm.

*Diameter.*—0.3 cm.

*Length of internodes.*—0.9-1.0 cm.

*Texture.*—Bifid hairs.

*Color of peduncle.*—RHS 138A.

*Length of peduncle.*—7.4 cm.

*Peduncle diameter.*—0.2 cm.

*Texture.*—Bifid hairs.

Inflorescence:

*Type.*—Compositae, solitary, semi-double type inflorescences borne terminally above foliage, ray and disc florets arranged on a capitulum.

*Quantity of short days to flowering* (*response time*).—Approximately 4.5 weeks.

*Natural season flowering.*—Mid to late September.

*Quantity of inflorescences per plant.*—120-130.

*Lastingness of individual blooms on the plant.*—About six weeks from first color.

*Fragrance.*—Slightly spicy.

Bud (when showing color):

*Color.*—RHS 61A.

*Length.*—0.8-0.9 cm.

*Width.*—1.0-1.1 cm.

*Shape.*—Oblate.

Immature inflorescence:

*Diameter.*—2.2 cm.

*Color of ray florets, upper surface.*—RHS 61A.

*Color of ray florets, lower surface.*—RHS 61A.

Mature inflorescence:

*Diameter.*—3.5-3.6 cm.

*Depth.*—1.5 cm.

*Total diameter of disc.*—0.5 cm.

*Receptacle color.*—RHS 144A.

*Receptacle height.*—0.3 cm.

*Receptacle diameter.*—0.4 cm.

Ray florets:

*Average quantity of florets.*—Between 120 and 130 in several whorls.

*Color of florets, upper surface* (*abaxial*).—RHS 61A.

*Color inner surface* (*adaxial*).—RHS 61A.
*Length.*—1.5-1.7 cm.
*Width/diameter.*—0.3 cm.
*Shape.*—Elliptical.
*Apex shape.*—Most obtuse and dentate.
*Base shape.*—Tube.
*Margin.*—Entire, small incisions may occur at the tip.
*Texture, upper surface.*—Papillate.
*Lower surface.*—Papillate.

Disc florets: 50
*Width.*—0.1 cm.
*Length.*—0.3 cm.
*Color.*—RHS 61B at apex, N144D at base.

Phyllaries:
*Quantity.*—20-25.
*Color, upper surface.*—RHS 137B.
*Color, lower surface.*—RHS 137C.
*Length.*—0.6-0.8 cm.
*Width.*—0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.3-0.5 cm.
*Style color.*—RHS 150B.
*Style length.*—0.3 cm.
*Stigma color.*—RHS 7D.
*Stigma shape.*—Bi-parted.
*Ovary color.*—RHS 145C.
*Ovary length.*—0.15 cm.
*Ovary width.*—0.1 cm.

Androecium:
*Stamens.*—1, found on only disc florets.
*Color of filaments.*—RHS 2C.
*Length filaments.*—0.2 cm.
*Anther color.*—RHS 13A.
*Anther length.*—0.2 cm.
*Anther shape.*—Oval to club shaped.
*Color of pollen.*—RHS 13A.
*Pollen amount.*—Moderate.
*Fertility/seed set.*—Fertile as male parent.
*Disease/pest resistance.*—Has not been determined to date.

What is claimed is:

1. A new and distinct variety of *Chrysanthemum* plant named 'CIFZ0067' substantially as illustrated and described herein.

* * * * *